US012653950B2

(12) United States Patent
Krietzman et al.

(10) Patent No.: US 12,653,950 B2
(45) Date of Patent: Jun. 16, 2026

(54) PREDICTIVE BIOLOGICAL HOMEOSTASIS

(71) Applicants: Mark H. Krietzman, Rolling Hills, CA (US); Wolfgang Renz, Rheinfelden (DE)

(72) Inventors: Mark H. Krietzman, Rolling Hills, CA (US); Wolfgang Renz, Rheinfelden (DE)

( * ) Notice: Subject to any disclaimer, the term of this patent is extended or adjusted under 35 U.S.C. 154(b) by 688 days.

(21) Appl. No.: 18/112,910

(22) Filed: Feb. 22, 2023

(65) Prior Publication Data

US 2023/0211083 A1 Jul. 6, 2023

Related U.S. Application Data

(63) Continuation of application No. PCT/US2021/047471, filed on Aug. 25, 2021, and a
(Continued)

(51) Int. Cl.
*A61M 5/172* (2006.01)
*G16H 20/17* (2018.01)

(52) U.S. Cl.
CPC .......... *A61M 5/1723* (2013.01); *G16H 20/17* (2018.01); *A61M 2230/201* (2013.01)

(58) Field of Classification Search
CPC ........ A61M 5/1723; A61M 2202/0486; A61M 2230/201; A61M 2210/08;
(Continued)

(56) References Cited

U.S. PATENT DOCUMENTS

2003/0236265 A1* 12/2003 Sayada ................ C07D 513/18
514/252.13
2006/0194221 A1 8/2006 Skurkovich et al.
(Continued)

FOREIGN PATENT DOCUMENTS

WO WO 2020/043708 A1 3/2020

OTHER PUBLICATIONS

"Marianne J Middelveen, Persistent Borrelia Infection in Patients with Ongoing Symptoms of Lyme Disease", Apr. 14, 2018, MDPI, pp. 1-40. (Year: 2018).*
(Continued)

*Primary Examiner* — Kevin C Sirmons
*Assistant Examiner* — Antarius S Daniel
(74) *Attorney, Agent, or Firm* — BAKER HOSTETLER LLP

(57) ABSTRACT

Sensor in signal communication with at least one controller measure at least blood glucose levels, galvanic skin response microsiemens, heart rate, oxygen and temperature of a subject. At least one controller induces an individualized hypoglycemic condition within a predetermined non-homeostatic blood glucose level. Controllers may be in signal communication with one or more computing devices. The controller may also be a computing device. The system fluidly controls flow control devices to control delivery of at least insulin and glucose. The fluid control devices are in signal communication with at least one microprocessor having memory A controller controls the fluid control devices for at least insulin glucose, and a treatment cocktail to keep blood glucose level (BGL) within a target non-homeostatic hypoglycemic range.

13 Claims, 7 Drawing Sheets

Related U.S. Application Data continuation of application No. PCT/US2021/047474, filed on Aug. 25, 2021.

(60) Provisional application No. 63/447,270, filed on Feb. 21, 2023, provisional application No. 63/069,998, filed on Aug. 25, 2020, provisional application No. 63/070,116, filed on Aug. 25, 2020.

(58) Field of Classification Search
CPC ...... A61M 2210/083; A61M 2210/086; A61M 2210/02
See application file for complete search history.

(56) References Cited

U.S. PATENT DOCUMENTS

| | | | | |
|---|---|---|---|---|
| 2011/0071464 | A1* | 3/2011 | Palerm ................ | A61M 5/1723 604/66 |
| 2015/0231172 | A1 | 8/2015 | D'Agostino et al. | |
| 2016/0174853 | A1* | 6/2016 | Cho ..................... | A61B 5/4261 600/301 |
| 2018/0117249 | A1* | 5/2018 | Pennington ......... | A61M 5/1723 |
| 2019/0008848 | A1 | 1/2019 | Zhang et al. | |
| 2021/0330750 | A1* | 10/2021 | Kampinga ........... | A61K 9/0019 |

OTHER PUBLICATIONS

Pothineni et al.; "Azlocillin can be the potential drug candidate against drug-tolerant Borrelia burgdorferi sensu stricto JLB31"; Scientific Reports; vol. 10, 3798; 2020; 15 pages.

Yadavalli et al.; "Standalone or combinatorial phenylbutyrate therapy shows excellent antiviral activity and mimics CREB3 silencing"; Science Advances; vol. 6; Dec. 2020; 11 pages.

International Patent Application No. PCT/US2021/047474; Int'l Written Opinion and Search Report; dated Jan. 31, 2022; 12 pages.

International Patent Application No. PCT/US2021/047471; Int'l Written Opinion and Search Report; dated Jan. 31, 2022; 12 pages.

* cited by examiner

PREDICTIVE BIOLOGICAL HOMEOSTASIS

CROSS-REFERENCE TO RELATED APPLICATIONS

This application is a By Pass Continuation of PCT/US2021/047471, filed Aug. 25, 2021 and PCT/US2021/047474, filed Aug. 25, 2021, both of which claimed priority to U.S. Provisional Patent Application Ser. No. 63/069,998, filed Aug. 25, 2020, entitled METHOD OF TREATMENT FOR PULMONARY INFLAMMATION; and to U.S. Provisional Patent Application Ser. No. 63/070,116, filed Aug. 25, 2020, entitled METHOD OF TREATMENT FOR INFLAMMATION, and this application claims priority to U.S. Provisional Patent Application Ser. No. 63/447,270, filed Feb. 21, 2023, entitled PREDICTIVE BIOLOGICAL HOMEOSTASIS, all of which are hereby incorporated by reference in their entirety.

FIELD OF THE DISCLOSURE

Systems and methods to control hypoglycemic conditions in a primate during therapeutic treatment of pathogens.

BACKGROUND

Abnormal cell populations either cancerous or pre-cancerous are often characterized by having increased glucose metabolism and/or abnormal cellular membranes more susceptible to degradation (either reversible or irreversible) when conditions of normal homeostasis are disrupted.

Certain pathogens such as Epstein Barr virus, herpes viruses, and Lyme disease caused by at least the bacterium *Borrelia Burgdorferi, Borrelia mayonii, Borrelia afzelii* and *Borrelia garinii* (extracellular pathogen transmitted to humans through the bite of infected ticks) can accumulate within the synovium. Lyme disease is extremely difficult to eradicate.

It is therefore a desideratum to reduce and remove populations of viruses, abnormal cell and harmful bacteria from subjects.

DISCLOSURE

Disclosed herein are aspects of devices, methods, and systems to measure and predict BGL from at least two inputs of blood glucose levels, galvanic skin response temperature and heart rate.

Disclosed herein are aspects of devices, methods, and systems to predict changes in at least BGL measure and predict BGL, from at least two inputs of blood glucose levels, galvanic skin response, pupillary response, temperature and heart rate, and maintain a subject in a safe hypoglycemic condition for a prolonged period of time.

Disclosed herein are aspects of devices, methods, and systems to use physiological levels to predict changes in BGL, the system and method configured to measure at least two inputs of blood glucose levels, galvanic skin response, oxygen saturation, pupillary response, temperature and heart rate and provide the data to a processor.

In some instances a controller, having at least a processor, receive measured physiological levels to constructs and/or refines a predictive model to at least one of set off an alarm if BGL are trending below a threshold. Said threshold may be fixed. Said threshold, in other instances, may be variable. In some instance the threshold or lower threshold is personalized based on data previously collected from a subject.

Aspects of a method to predictively maintain hypoglycemic conditions are disclosed herein including measuring blood glucose levels overtime in a subject after the subject ingests a predetermined quantity of a known quality sugar in a predetermined form with a known glycemic level and measuring galvanic skin response (GSR) overtime in the subject after the subject ingests the predetermined quantity of a known quality sugar in a predetermined form with a known glycemic level. Then constructing a look up table for the subject's metabolic levels based on collected data. Inducing a hypoglycemic condition in a subject within a target BGL range by way of using insulin and glucose. Monitoring BGL and at least GSR of the subject with one or more sensors in signal communication with a controller and the controller is figured to use the sensor data to predictively control the subject's BGL by way of infusion of insulin and at least glucose to maintain the target hypoglycemic level or range without exceeding a lower threshold.

In some instances the controller controls the administration of at least one of oxygen and hydrogen. Income instances oxygen saturation is measured and also used to predictively maintain the hypoglycemic level target. In some instances the controller administers magnesium before or during administration of glucose.

Disclosed herein are aspects of devices, methods, and systems of control to predictively maintain a subject in a predetermined hypoglycemic condition for a prolonged period of time.

Disclosed herein are aspects of devices, methods, and systems of maintaining viability of a subjects while keeping said subject in a prolonged non-homeostatic condition to reduce bacterial cell populations in a primate.

Disclosed herein are aspects of devices, methods, and systems of maintaining viability of a subject while keeping said subject in a prolonged non-homeostatic condition to reduce viral populations in a primate.

Disclosed herein are aspects of devices, methods, and systems of maintaining viability of a subject while keeping said subject in a prolonged non-homeostatic condition to reduce abnormal cell populations in a primate.

Disclosed herein are aspects of devices, methods, and systems of disrupting cellular homeostasis and both avoiding coma and keeping a subject in a prolonged hypoglycemic condition.

Disclosed herein are aspects of devices, methods, and systems of reducing infection by bacteria or virus. In some exemplary implementations aspects include placing a primate subject cells in hypoglycemic conditions to increase cell membrane permeability to at least one antibiotic compound which also can be referred to as "cocktail" or "cocktail components".

In some exemplary implementations aspects include maintaining hypoglycemic conditions in a primate to increase permeability of synovial membranes to allow passage of the antibiotics into the synovial space and/or fibroblast-like synoviocytes (FLSs), of an antibiotic or cocktail.

Disclosed herein are aspects of devices, methods and systems for drug development and testing under hypoglycemic conditions. The method further comprising delivering one of a supplement and a pharmaceutically effective dose of antibiotics to a population of bacterial in an animal model which has been selectively placed in a controlled hypoglycemic condition. In some cases, the animal model is a primate. In some cases, the animal model is a humanized non-primate, in some cases the animal model is a non-primate mammal.

Disclosed herein are aspects of devices, methods, and systems of delivering one of a supplement and a pharmaceutically effective dose of one or more antibiotics to a population of bacteria in a primate, the primate selectively placed in a controlled hypoglycemic condition whereby death of the bacteria occurs at a higher rate than death of the same bacteria under non hypoglycemic conditions.

Disclosed herein are aspects of devices, methods, and systems of delivering a phased or sequenced series of cocktail compounds, forming a pharmaceutically effective dose, to cause death in bacteria or viruses when the primate is under a controlled hypoglycemic conditions.

In the above exemplars one or more controllers control hypoglycemic conditions in the test animal or primate via data received from two or more sensor inputs whereby fluid control devices to control the flow of insulin, glucose and optionally additional cocktail component and adjuvants and/or oxygen.

Aspects of the delivery systems, control system and methods disclosed include a control system are configured to maintain a subject in a controlled hypoglycemic condition and automatically adjust. Condition to maintain the hypoglycemic condition within a target range of blood glucose levels (BGL) and above a first threshold. In some instances, the system includes logic to raise BGL when the first threshold or a lower second threshold is reached. The thresholds and ranges may be personalized based on collected individual data about a patient prior to treatment with the hypoglycemic method disclosed herein.

Aspects of the delivery systems, control system and methods disclosed include a control system are configured to maintain a subject in a controlled hypoglycemic condition and automatically adjust. Condition to maintain the hypoglycemic condition within a target range of blood glucose levels (BGL) and galvanic skin response (GSR) and above a first threshold. In some instances, the system includes logic to raise BGL when the first threshold or a lower second threshold is reached. The thresholds and ranges may be personalized based on collected individual data about a patient prior to treatment with the hypoglycemic method disclosed herein.

Aspects of the delivery systems, control system and methods disclosed include a control system are configured to maintain a subject in a controlled hypoglycemic condition and automatically adjust. Condition to maintain the hypoglycemic condition within a target range of blood glucose levels (BGL) and galvanic skin response (GSR) and at least one of heart rate and temperature above a first threshold. In some instances, the system includes logic to raise BGL when the first threshold or a lower second threshold is reached. The thresholds and ranges may be personalized based on collected individual data about a patient prior to treatment with the hypoglycemic method disclosed herein.

The system and method include, but are not limited to obtain and storing baseline data for a subject who is in a homeostatic state including one or more of:

A. Measuring the normal level of the subject's insulin which may include blood glucose levels over a period of between 15 minutes and 48 hours before administering any hypoglycemic protocols and measuring at least one of the subjects pretreatment GSR, temperature and heart rate over a period of between 15 minutes and 48 hours before administering the hypoglycemic protocols. Measurement may be done by one or more sensors. Said sensors may be disposable. Said sensor may be wired to a controller or connect through wireless protocols to a controller.

B. Preparing a subject specific algorithm in the form of computer code stored in memory and configured to be used in a microprocessor in signal communication with one or more controllers configured to maintain a subject in a prolonged hypoglycemic condition above a low threshold and below a high threshold based on the data collected before administering hypoglycemic protocols. The system and method include, but are not limited to using stored baseline data for the subject and controlling at least insulin delivery to disrupt BGL homeostasis and maintain a prolonged hypoglycemic state in the subjects during therapeutic administration.

C. During administration of hypoglycemic protocols to disrupt homeostatic BGL in the subject said subject in some instances is monitored with sensors in signal communication to one or more controller providing measurements of two or more of the subject's vital signs, including but not limited to, heart rate (HR), blood pressure (BP), electrocardiogram (EKG), electroencephalogram (EEG), oxygen saturation ($O_2$), galvanic skin response (GSR), skin moisture, pupillary dilation (PD), temperature (T), respiration (R) rate, and blood glucose level (BGL).

D. During administration of hypoglycemic protocols to disrupt homeostatic BGL in the subject in some instances at least two of the subject's vital signs subject of heart rate (HR), temperature, galvanic skin response (GSR), skin moisture, pupillary dilation and blood glucose level (BGL) are monitored with one or more sensors in signal communication with a controller.

E. During administration of hypoglycemic protocols to disrupt homeostatic BGL in the subject some instances at least one controller controls administration of at least boluses of insulin (via one or more devices) to place the subject in a temporarily hypoglycemic condition at one of a predetermined target range and above a predetermined low hypoglycemic threshold. The frequency of administration and the quantity may be controlled. During administration of hypoglycemic protocols to disrupt homeostatic BGL in the subject some instances at least one controller controls administration of at least boluses of insulin and glucose to place the subject in a temporarily hypoglycemic condition at one of a predetermined target range and above a predetermined low hypoglycemic threshold. The frequency of administration and the quantity may be controlled.

The controller(s) may be configured to use sensor data to control at least one of control the amount and the rate of insulin delivery to keep subject to maintain blood glucose levels (BGL) within a defined range corresponding to the target non-homeostatic BGL hypoglycemic condition for the subject. In some instances, the target hypoglycemic condition for the subject is related to or arise from the previously measured levels for that subject. In some instances, if measured oxygen saturation is below a predetermined level the controller administers additional to the subject. Optionally one or more alarms are generated via the controller(s) if the controlled BGL in the subject (as measured by the sensors) are outside of a range selected for the subject at a given time during treatment or BGL is predicted to fall below a minimum level for the subject. The alarms may be any form including but not limited to visual, auditory, and haptic. The alarms may at least one of interrupt the insulin delivery, cause glucose to be delivered, cause oxygen to be delivered until vital signs are restored to within the target range. Optionally pharmaceutically effective amounts of at least one of an antihistamine and an antiemetic may be administered prior to insulin delivery. After the subject is in the hypoglycemic condition the devices and systems sequence administration of pharmaceutically effective amounts of the treatment compound or cocktail in a pharmaceutically effective dose, under hypoglycemic conditions.

Optionally, also measuring at least one of the subject's vital signs, including but not limited to ECG, EKC, blood pressure, heart rate, temperature, oxygen saturation, and over a period of between 15 minutes and 48 hours before treatment and collecting said data. Optionally one or more alarms configured in the computer code are configured so that the controller(s) generates an alarm if measured vital sign(s) is outside a predefined range. In some instances, using the previously measured vital sign data to set said range. The alarms may at least one of interrupt the insulin delivery, cause glucose to be delivered, cause oxygen to be delivered until vital signs are restored to within the target range. In some instances, a predetermined interval during homeostatic measurements the subject consumes a known quality sugar in a predetermined form with a Glycemic Index (GI) and a known glycemic load (GL). By supplying a consistent food type of a fixed quantity and with a known GI and GL the measurement of the subject's innate systems response to the consumed material can be measured via blood glucose monitoring, and used at least in part, as a data point to set the target range for hypoglycemic conditions for that subject's treatment.

In some instances, prior to hypoglycemic protocols at a predetermined interval the subject consumes a known quality sugar in a predetermined form with a known GI and GL. By supplying a food type of a fixed quantity and with a known GI and GL the controller can use look up tables (LUT) or refer to prior measurements of the subject's consumption of the same GI and GL food and used, at least in part, as a data point when maintaining the target range for hypoglycemic conditions for that subject.

Disclosed herein are aspects of devices, methods, compositions of matter and systems to induce a hypoglycemic condition within a predetermined blood glucose range for treating infections including bacterial and viral cells (including but not limited to herpes) including one or more controllers in signal communication with at least a BGL and one or more sensors which measure an aspect that is physiological and in signal communication with one or more fluid flow control devices to control deliver of at least insulin and glucose and at least one cocktail containing at least one of antibiotic and antiviral components. The fluid control devices are in signal communication with at least one microprocessor having memory and the one or more physiological sensors, one or more databases or lookup tables and, wherein the controller controls the fluid control devices for at least insulin glucose, and the cocktail to keep blood glucose level (BGL) within a target hypoglycemic range for BGL for the patient. In some instances, the controller receives sensor data inputs and adjust the hypoglycemic target range for BGL in response to sensory data received.

The sensor data is two or more of BGL, heart rate, pupillary dilation, galvanic skin response, and temperature. In some instances, the controller controls the administration of at least one of oxygen and hydrogen.

Disclosed herein are aspects of controllers in signal communication with said sensors which measure two or more physiological conditions in the subject and are in signal communication with one or more fluid flow control devices to control deliver of at least insulin and glucose and at least one cocktail containing therapeutic components. The fluid control devices are in signal communication with at least one microprocessor having memory and the physiological sensors, one or more databases or lookup tables and, wherein the controller controls the fluid control devices for at least insulin glucose, and the cocktail to keep blood glucose level (BGL) within a target hypoglycemic range for BGL for the patient.

In some instances, the controller receives sensor data inputs and adjust the hypoglycemic target range for BGL in response to sensory data received. In some instances, the sensor data is two or more of BGL, oxygen saturation, pupillary dilation, heart rate, galvanic skin response, and temperature.

Disclosed herein are aspects of devices, methods, and systems of reducing cancer or abnormal cells in a primate. In some exemplary implementations' aspects include placing a primate subject's cells in hypoglycemic conditions to increase abnormal cells or cancer cell membrane permeability to at least one chemotherapeutic agents which also can be referred to as "cocktail" or "cocktail components".

Disclosed herein are aspects of devices, methods, and systems of reducing cancer or abnormal cells in a primate. In some exemplary implementations' aspects include placing a primate subject's cells in hypoglycemic conditions to increase abnormal cells or cancer cell membrane permeability to at least one adjuvant for chemotherapeutic agents.

Disclosed herein are aspects of devices, methods, and systems of disrupting cellular homeostasis to maintain prolonged hypoglycemic conditions to disrupt the homeostasis of synovial membranes including a controller receiving blood glucose levels (BGL) measurements from a sensor on a subject. The controller controlling delivery of insulin to the subject to lower blood glucose level measurements to a target non-homeostatic hypoglycemic range. The controller controlling delivery of glucose to the subject to maintain blood glucose levels within an optimal non-homeostatic hypoglycemic range. Whereby the synovial membranes of the subject become more permeable to antibiotics used to treat Borreli; and, the controller controlling delivery of a cocktail of antibiotics to treat Borreli, when the subject's BGL is determined to be within the target non-homeostatic hypoglycemic range. In some instances the antibiotics are at least one of but are not limited to clarithromycin, doxycycline, metronidazole. mezlocillin, piperacillin, azlocillin acylampicillin, cefuroxime, and Ceftriaxone.

In some instances the target non-homeostatic hypoglycemic range for BGL is 30 mg/dl to less than about 50 mg/dl. In some instances the controller controlling delivery of at least one of glucose and insulin is configured to lower blood glucose level measurements to an optimal non-homeostatic hypoglycemic range between about 30 mg/dl and about 38 mg/dl. In some instances an adjuvant from the group including but not limited to Quercetin and Curcumin is added. In some instance the amount of insulin required to reach target non-homeostatic hypoglycemic range is reduced by adding an antihistamine before or during antibiotic delivery. In some instances the antibiotics are sequenced in time with each antibiotic administered separately before the next antibiotic is administered.

Alarms: In some instances if the BGL is below the target non-homeostatic hypoglycemic range the controller is configured to trigger an alert or alarm and in some instances the alarm at least one of interrupt the delivery of insulin, delivers glucose, and delivers oxygen.

Galvanic Skin Response: In some instances, the controller receives galvanic skin response (GSR) measurements from a sensor on a subject; and, the controller controlling delivery of insulin and glucose alters the amount or rate of insulin or glucose being delivered based on at least in part GSR measurements. In some instances, the controller receives heart rate galvanic measurements from a sensor on a subject and, the controller controlling delivery of insulin and glucose alters the amount or rate insulin or glucose is delivered based on at least in part GSR and heart rate measurements. In some instances an observer checks pupillary dilation size before insulin is administered based on the periodic observer during prolonged hypoglycemic conditions the observer overrides the controller and at least one of one of insulin administration is reduced, insulin administration is stopped, and glucose is administered.

Pupillary Dilation: In some instances an observer checks pupillary dilation size and inputs a value based on observation into the controller and, the controller controlling delivery of insulin and glucose alters at least one of the insulin and glucose being administered based on at least in part on the pupillary value input. In some instances machine vision periodically measures subject's pupillary change in size during prolonged hypoglycemic conditions which is input to the controller and, the controller controlling delivery of insulin and glucose alters at least one of the insulin and glucose being administered based on at least in part on pupillary size inputs.

Disclosed herein are aspects of devices, methods, and systems of disrupting cellular homeostasis to maintain prolonged hypoglycemic conditions to disrupt the homeostasis of synovial membranes including a controller receiving blood glucose levels (BGL) measurements from a sensor on a subject. The controller controlling delivery of insulin to the subject to lower blood glucose level measurements to a target non-homeostatic hypoglycemic range. The controller controlling delivery of glucose to the subject to maintain blood glucose levels within an optimal non-homeostatic hypoglycemic range. Whereby the synovial membranes of the subject become more permeable to antiviral agents used to treat Herpes; and, the controller controlling delivery of a cocktail of antiviral agents to treat Herpes, when the subject's BGL is determined to be within the target non-homeostatic hypoglycemic range. In some instances the antivirals are at least one of but are not limited to antiviral agents are at least one of but are not limited to Acyclovir, Famciclovir, Valacyclovir and phenylbutyrate (PBA).

Disclosed herein are aspects of devices, and systems of disrupting cellular homeostasis to monitor hypoglycemic conditions in a subject, including a controller receiving a sensor body with an adhesive interface on one side of the sensor body. The sensor body includes a blood glucose sensor and at least one additional sensor of more a galvanic skin response sensor, a temperature sensor, a heart rate sensor and, a transmitter. In some instance the transmitter communicates with and provides data input to a computing device. In some instances the computing device acts as a controller of the infusion of at least one of glucose and insulin.

It is appreciated by those skilled in the art that some of the circuits, components, controllers, modules, and/or devices of the system disclosed in the present application are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical such as, for example, conductive wires, electromagnetic wave guides, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying analog and/or digital formats without passing through a direct electromagnetic connection. These information paths may also include analog-to-digital conversions ("ADC"), digital-to-analog ("DAC") conversions, data transformations such as, for example, fast Fourier transforms ("FFTs"), time-to-frequency conversations, frequency-to-time conversions, database mapping, signal processing steps, coding, modulations, demodulations, etc. The controller devices and smart devices disclosed herein operate with memory and processors whereby code is executed during processes to transform data, the computing devices run on a processor (such as, for example, controller or other processor that is not shown) which may include a central processing unit ("CPU"), digital signal processor ("DSP"), application specific integrated circuit ("ASIC"), field programmable gate array ("FPGA"), microprocessor, etc. Alternatively, portions DCA devices may also be or include hardware devices such as logic circuitry, a CPU, a DSP, ASIC, FPGA, etc. and may include hardware and software capable of receiving and sending information. The sensors may be removable, wearable, reusable or disposable. One sensor module may contain multiple sensors.

FIGURES

The disclosure may be better understood by referring to the following figures. The components in the figures are not necessarily to scale, emphasis instead being placed upon illustrating the principles of the invention. In the figures, like reference numerals designate corresponding parts throughout the different views.

Figure 5:
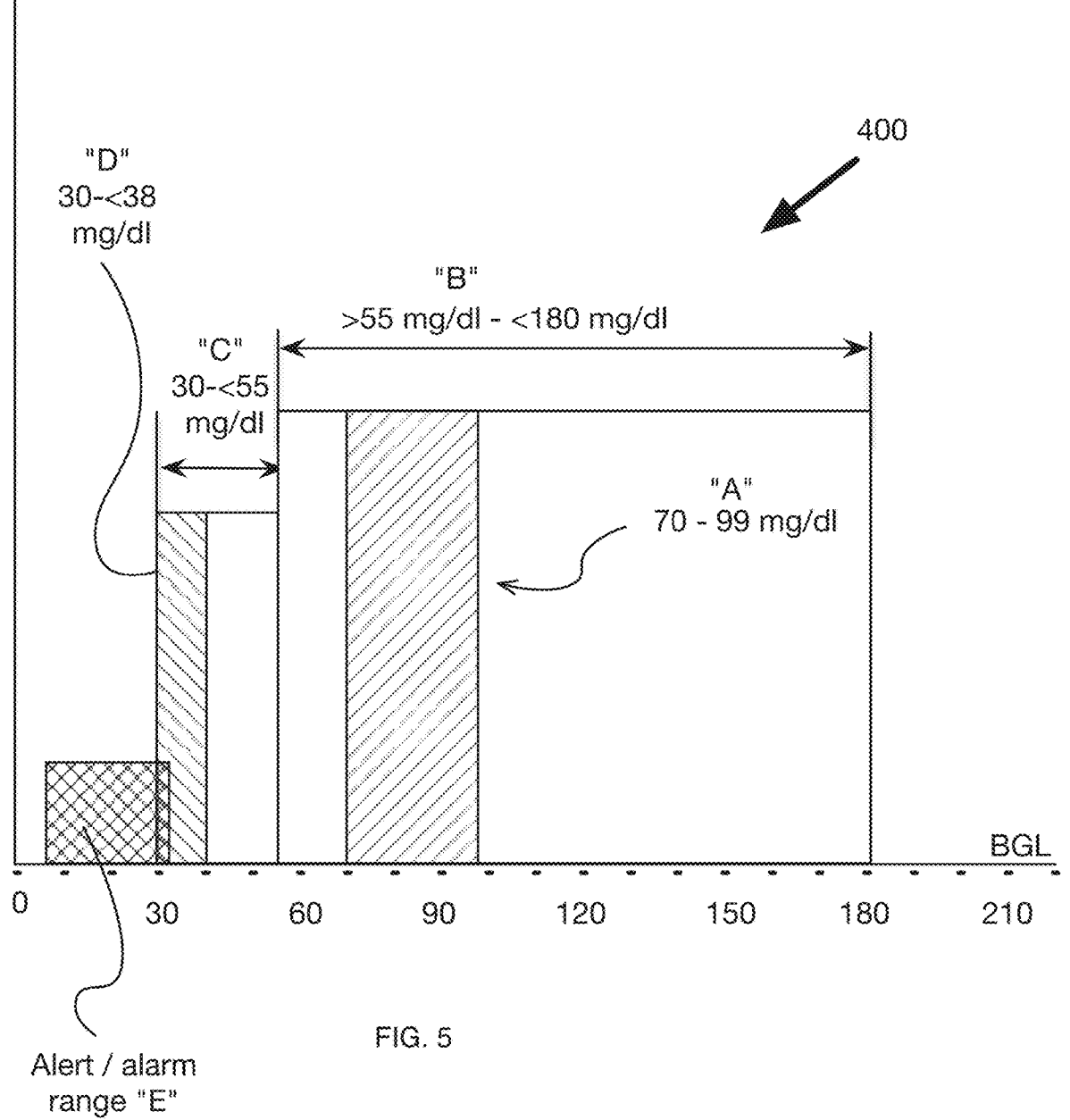

FIG. 5 spectrum of blood glucose levels and hypoglycemic range.

Figure 6:
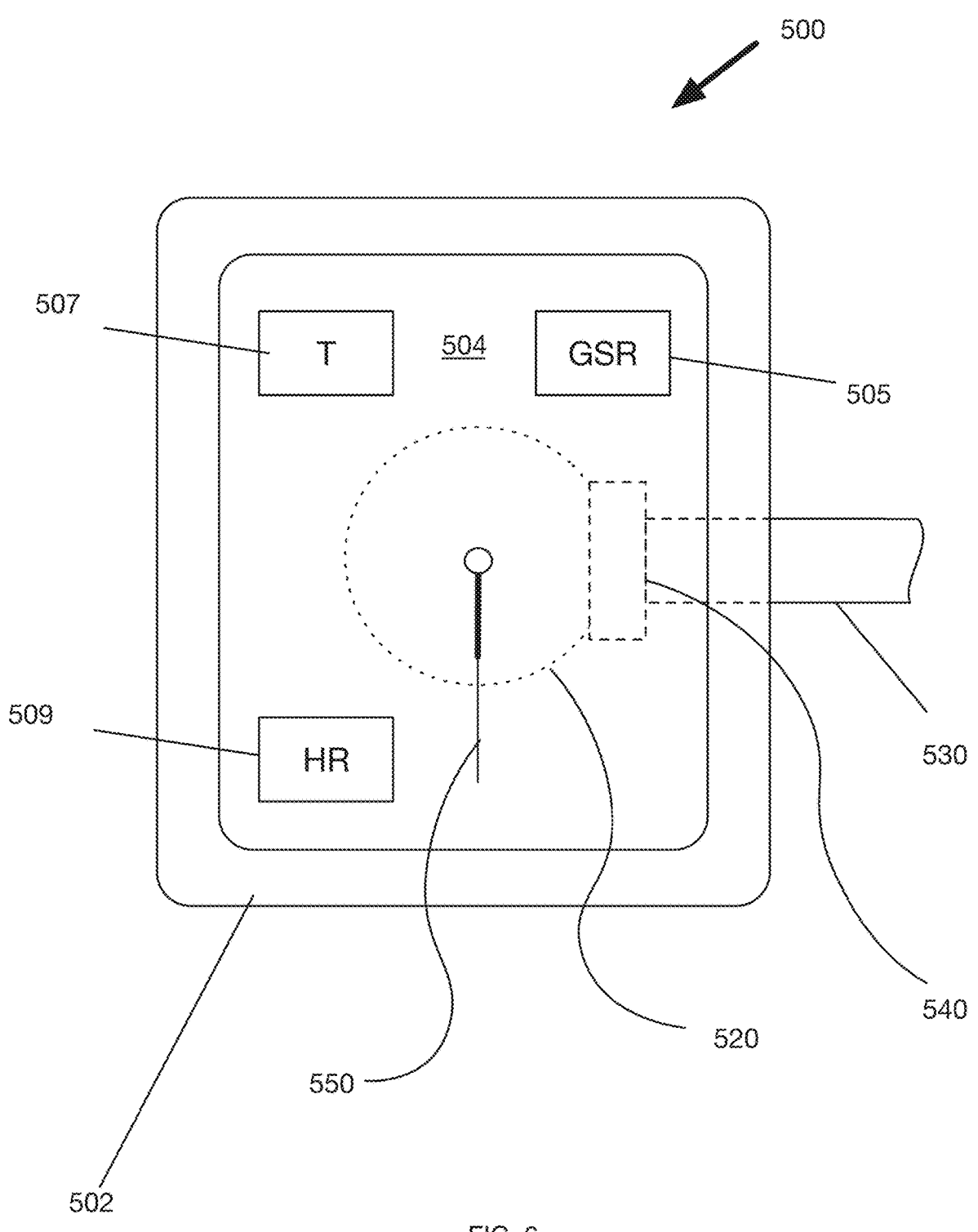

FIG. 6 is an illustration of aspects of a sensor.

Figure 7:
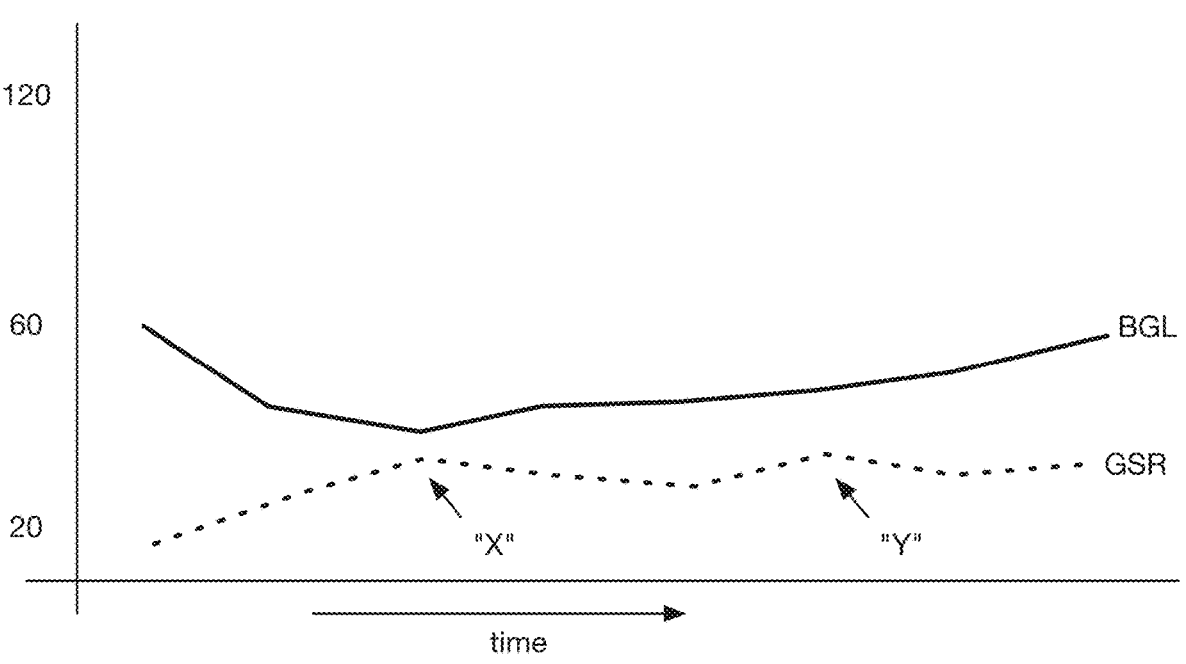

FIG. 7 is a graphical illustrations of aspects of some changes in metabolic measurements during controlled hypoglycemic protocols.

Figure 8:
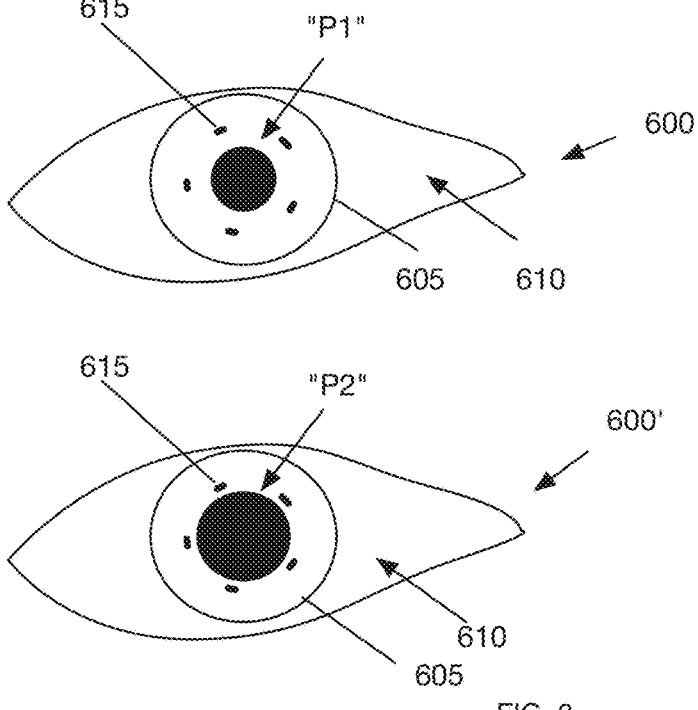

FIG. 8 is an illustrations of aspects of pupillary changes during controlled hypoglycemic protocols.

All descriptions and callouts in the Figures and all content of any referenced citation are hereby incorporated by this reference as if fully set forth herein.

FURTHER DISCLOSURE

The compositions disclosed herein can be included in a pharmaceutical or nutraceutical composition together with additional active agents, carriers, vehicles, excipients, or auxiliary agents identifiable by a person skilled in the art upon reading of the present disclosure, and such compositions are within the scope of this disclosure. All publications cited herein are hereby incorporated by reference as if fully set forth herein.

The pharmaceutical or nutraceutical compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds and/or adjuvants can also be incorporated into the compositions. A pharmaceutical composition is formulated to be compatible with its intended route of administration.

Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, primate, dog, cat, and rabbit) and most preferably a human. Administration by inhalation, the gas or gases are delivered orally.

As used herein a "primate subject" is defined to include a monkey, baboon, chimpanzee, gorilla, and a human. Non-human primates are appreciated to themselves be susceptible to infection by retroviruses and in particular immunodeficiency viruses and represent well-established animal models as to human response with an appreciation that physiological differences often require different doses in milligrams per kilogram for a nonhuman primate animal model relative to a human.

Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, primate, dog, cat, and rabbit) and most preferably a human.

A pharmaceutically effective dose (ED) or effective concentration (EC) is a dose or concentration of an element (such as hydrogen), a phytochemical, compound ore drug that produces a biological response. The term effective dose is used when measurements are taken in vivo, while the term effective concentration is used when the measurements are taken in vitro. This is generally defined by the range between the minimum effective dose (MED) and the maximum tolerated dose (MTD). The MED is defined as the lowest dose level of a pharmaceutical product that provides a clinically significant response in average efficacy, which is also statistically significantly superior to the response provided by the placebo. Similarly, the MTD is the highest possible but still tolerable dose level with respect to a pre-specified clinical limiting toxicity. In general, these limits refer to the average patient population.

Plasma glucose levels are maintained within a narrow range by the pancreatic hormone's glucagon and insulin. A normal level threshold for BGL is about 140 mg/dL Hypoglycemia, is general a BGL of below 50 mg/dl in a non-diabetic and it triggers secretion of glucagon by pancreatic α cells, which promotes glycogenolysis and gluconeogenesis in the liver, and lipolysis in adipose tissue. On the other hand, hyperglycemia triggers secretion of insulin from pancreatic β cells, which promotes glucose uptake for energy production and anabolic processes such as glycogen synthesis and lipogenesis in the liver, muscles, and adipose tissue.

We have observed that controlled hypoglycemic conditions applied to patients via an infusion of insulin during combined with administration of a cocktail is associated with preferential reduction in *Borrelia*. The term cocktail refers to one or more of antibiotics and may include supplements and adjuvants. In some instances, the administration of the cocktail during controlled hypoglycemic conditions results in higher intercellular concentrations of cocktail therapeutics in cells then without hypoglycemic conditions. Many effective antibiotics are unsuccessful in penetrating the synovial membrane when administered at a MED and without hypoglycemic conditions approach of exceed their MTD. Our controlled hypoglycemic conditions are configured to reduce the MED whereby the cocktail is administered at below the MTD for cocktail components and can achieve effective therapeutic doses to reach bacteria within synovial membrane. The system hardware, software, microprocessors, and controllers are configured to adjust the administration (rate and quantity) of insulin to maintain controlled hypoglycemic conditions for an individual patient based on previously collected patient data. The system hardware, software, microprocessors, and controllers may set off alarms if blood glucose is outside a subject's predetermined range. The system hardware, software, microprocessors, and controllers are configured to control the infusion of glucose (rate and quantity), oxygen (rate and quantity) and cocktail components (rate and quantity of each) and set off alarms if at least two measured physiological vital signs such as blood glucose, GSR, temperature, SPO2 (oxygen saturation), heart rate are outside predetermined ranges or levels.

The system hardware, software, microprocessors, and controllers are configured to adjust the insulin administration to maintain controlled hypoglycemic conditions for an individual patient based on previously collected patient data which is used to define an individual target range for and define at least a first BGL lower threshold for that individual. In some instances, that data collected is also used to define a second lower BGL (also known as an alarm level) for that individual.

The system hardware, software, microprocessors, and controllers may override the target for blood glucose target range or first or second threshold levels of a patient based on one or more inputs of sensor data. The microprocessor compares the patient sensor data being collected in real time during hypoglycemic conditions with one or more of a look up table based on human physiology, a look up table (LUT) based on measurements of the patient made prior to treatment, threshold level preset in a decisioning module, and if one or more sensor measurements exceed a risk level a target range or threshold limit may be altered and the controller will then administer an effective amount of insulin or glucose (for example) to raise or lower the BGL to the revised or altered target range or above a revised threshold. The system can override the continuation of insulin administration or reduce the amount given. The system can add glucose to the patient, the system can add oxygen to the patient and the system can adjust infusion of cocktail components to the patient. In some instances, an alarm will be set-off if the sensor data exceeds a threshold. The previous collection of patient data may be over 15 minutes or more but preferably over several hours or over a day.

A simplified overview is that an in vivo animal model having an infection of *B. burgdorferi* is given a bolus of insulin, the cellular insulin receptors (IR) activate expecting sugar instead the insulin is followed by cocktail components. Synoviocytes, express a large number of insulin receptors and under hypoglycemic conditions will allow for a higher concentration of cocktail components to enter the synovium then would enter when the primate blood glucose levels (GL) are at normal levels. *B. burgdorferi* DNA has been detected in synovial fluid from up to 85% of patients with Lyme arthritis.

Epstein Barr Virus (Epstein-Barr virus (EBV), like all herpesviruses can establish latent infection within specific tissues, which are characteristic for each virus. Herpes virus 4 has been shown to accumulate in synovium. The synovium appears pale pink in color and architecturally covers all surfaces of the joint Synovial fluid is often referred to as an ultrafiltrate of the plasma.

A simplified overview is that an in vivo animal model having an infection of for example (and not as a limitation) *Borrelia* or a herpes is given controlled boluses of insulin, the cellular insulin receptors (IR) activate expecting sugar instead the insulin is followed by cocktail components. Ganglion roots express insulin receptors and under controlled hypoglycemic conditions will allow for a higher concentration of cocktail components to enter the root ganglia then would enter when the blood glucose levels (BGL) are at normal levels. This is advantageous as the ability of herpes simplex virus type 2 (HSV-2) to establish latency in and reactivate from sacral dorsal root sensory ganglia is the basis for recurrent genital herpes.

Figure 1:
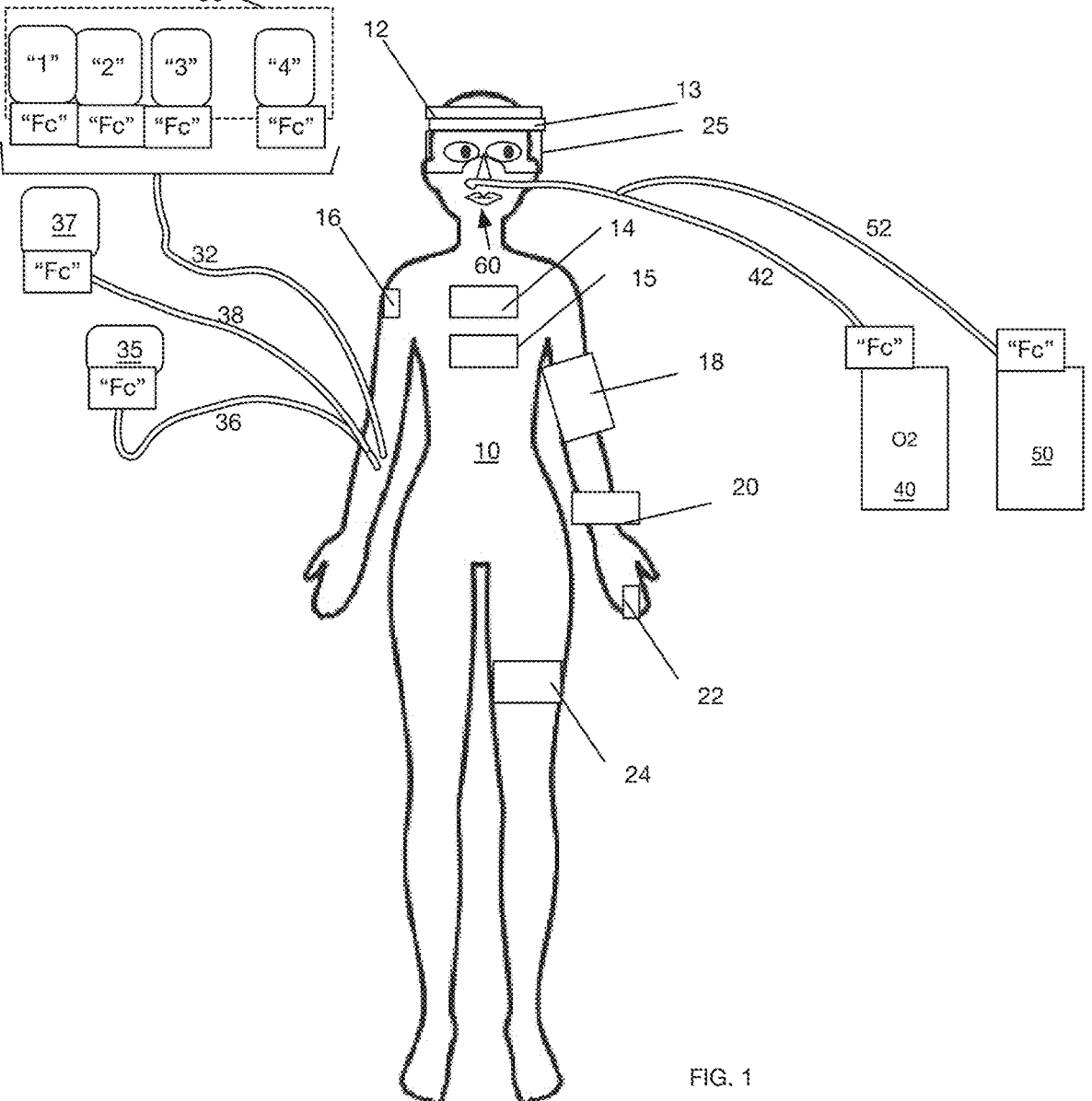
FIG. 1 is a diagram of a subject with sensor.
Figure 2:
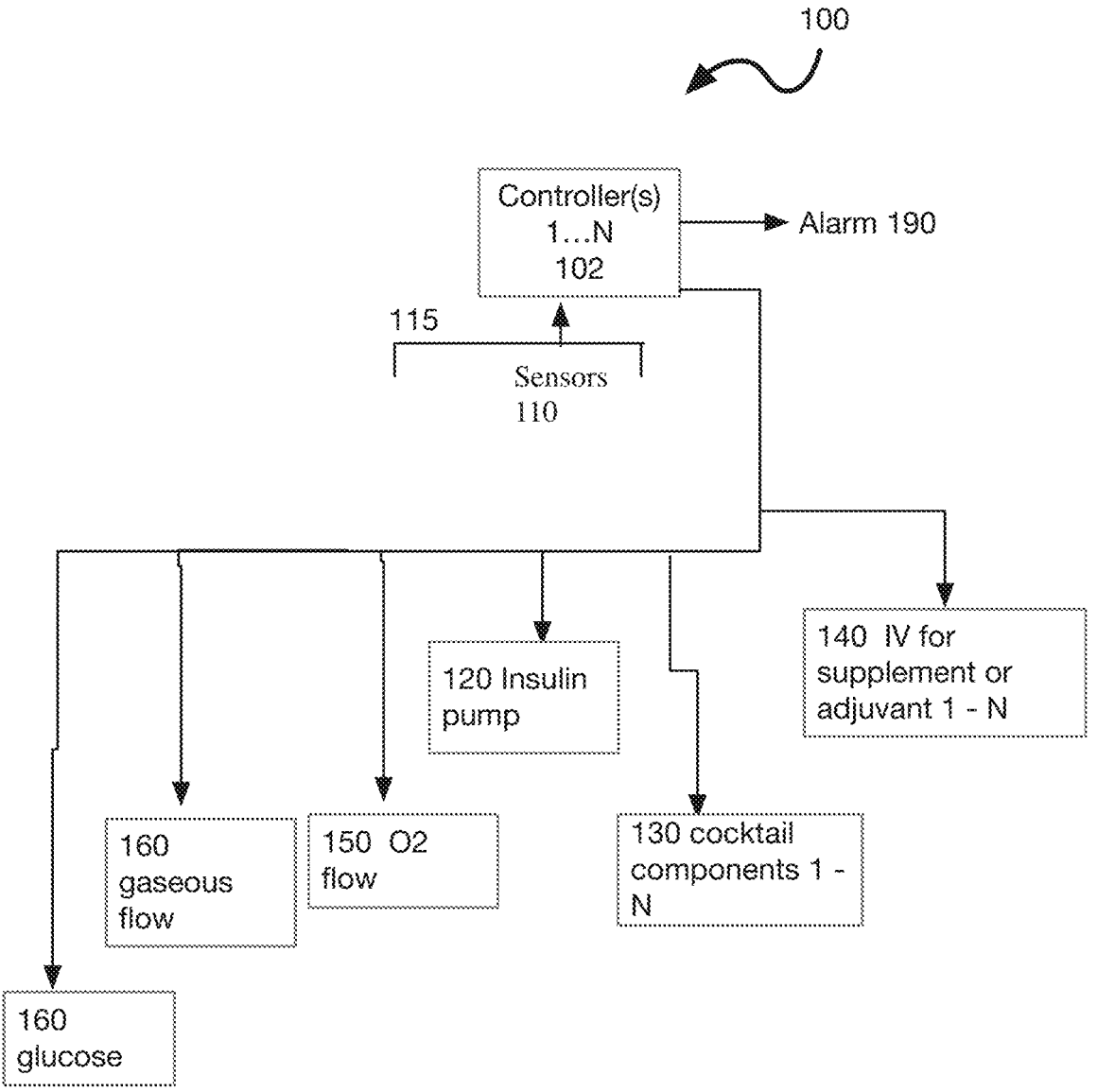
FIG. 2 is a diagram of a system overview.

In another simplified overview set forth in FIGS. 1 and 2 in which a primate 10 is connected to sensors 110 which are in signal communication with a controller 102. The primate is connected to or measured by a multitude of sensors 110. Including but not limited to sensors to measure temperature 12, EEC 13, EKG 14, galvanic skin response (which measured sweatiness) 15, blood glucose levels (BGL) 16, blood pressure 18, heart rate 20, oxygen saturation 22, temperature and additional measurements may include cortisol level measurements 24. Pupillary response is measured by observation and/or machine vision optical system 25. Cocktail components 30 (1–N) each in a containment vessel are connected to the patient or subject via fluid pathways and the fluid pathways each have a flow control device "fc" to start, stop and regulate the fluid flow, flow control devices include but are not limited to remotely controlled syringe pumps, peristaltic IV pumps, piston driven pumps and valves. Fluid control devices ("fc") are in signal communication with one or more controllers wherein the fluid flow rate is controlled in response to microprocessor control which in turn is based at least in part on sensor data received and analyzed by the system processors.

The cocktails components are connected to the patient via a fluid communication pathway 32. An insulin source 35 in a containment vessel has a flow control device "fc" in signal communication with a controller and is connected to the patient via a fluid communication pathway 36. A glucose source 37 in a containment vessel has a flow control device "fc" in signal communication with a controller and is connected to the patient via a fluid communication pathway

38. An oxygen source 40 in a containment vessel has a flow control device "fc" in signal communication with a controller and is connected to the patient via a fluid communication pathway 42. A second gaseous fluid source 50 in a containment vessel has a flow control device "fc" in signal communication with a controller and is connected to the patient via a fluid communication pathway 52. The second gaseous fluid source includes but is not limited to hydrogen, oxyhydrogen, and vaporized or atomized cannabinoids. Oral ingestion via the mouth 60 may be an alternative for some of the cocktail components or optional compounds.

A control system overview 100 is a simplified diagram showing one or more controllers 102 in signal communication 115 with the sensor 110 outputs. The controller processes the data from the sensors and decisions, based on LUTs, predetermined ranges for a patient and threshold levels to control at least insulin rate of administration and quantity. The controller also controls the administration of cocktail components 130. The controller 102 also controls the administration of supplement or adjuvant components 140. The controller 102 can also controls the administration of oxygen 150. The controller can also control the flow of gaseous fluids 160 such as hydrogen and oxyhydrogen. The controller 102 can also controls the administration of glucose 37. The controller also triggers or sets alarms 190 for out of threshold or range measurements. Normally when blood glucose level reach less than 30 mg/dl the system will administer a controlled release of glucose, at a rate based on sensor data, and within a predetermined first threshold (or safe limit). The system is configured for the individual and to avoid a significant glucose deficit which may impair brain function. The controller may be part of a computing device such as a smartphone, laptop computer or tablet computer.

In those instances, wherein levels fall below a second threshold which is below the first threshold alarms 190 will signal the and the system can administer magnesium to allow for an increased rate of glucose infusion. If glucose is infused too fast physiological stress is created in the vein and cramping. By adding magnesium, a higher flow of glucose can be used to restore the patient above the second threshold. Post treatment after patient stabilized and has BGL above a premeasured and predetermined base level (generally about 15-20 minutes) an oral infusion of at least 250 cc Glucose 40% and also a glucose-based fluid or juice such Coke and/or Apple juice at 500 cc orally helps the patient to maintain blood glucose levels.

Figure 3:
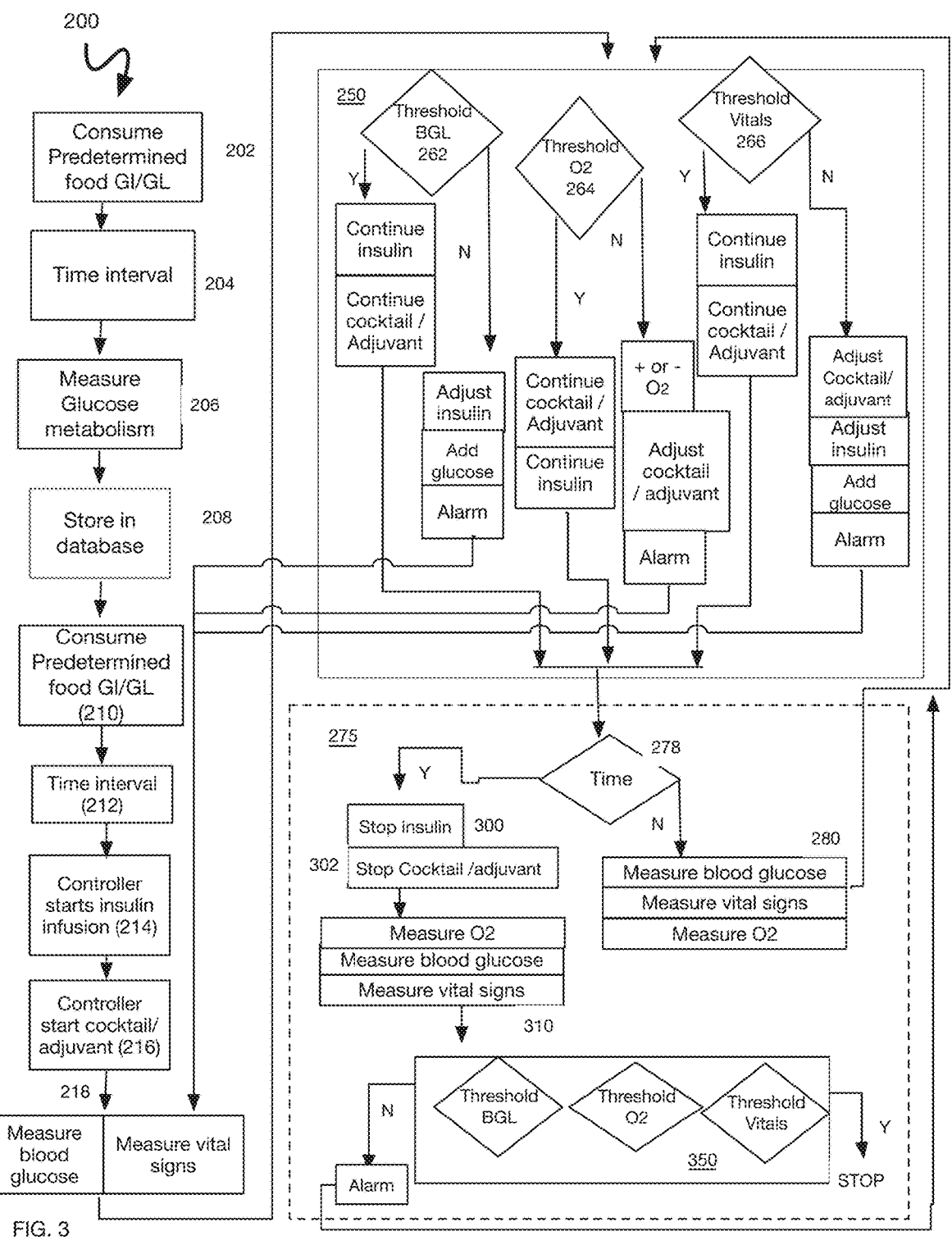
FIG. 3 is a flow diagram for the delivery system.

FIG. 3 illustrates an overview of the operational flow of the control system 200. Baseline or nominal homeostatic values for a subject's BGL, galvanic skin response, temperature, heart rate and $O_2$ saturation are collected. The collection follows administration of a predetermined quantity of a known quality sugar in a predetermined form with a known GL 202. During a time, interval 204 the subjects's blood glucose levels are measured 206 and the subjects galvanic skin response, temperature, heart rate and $O_2$ saturation are collected and the measurements are stored in a database 208.

In some instances a threshold hypoglycemic levels of metabolic activity are collected for a subject following administration of a predetermined quantity of a known quality sugar in a predetermined form with a known GL 202. During a time interval 204 insulin is added, the subjects's blood glucose levels are measured 206 and at least one of the subject's galvanic skin response, temperature, heart rate and $O_2$ saturation are measured and the measurements are stored in a database 208 to be used in fine tuning prolonged hypoglycemic conditions.

Prior to treating a subject with hypoglycemic protocols disclosed herein and/or the disclosed cocktail, the subject consumes once again the predetermined quantity of a known quality sugar in a predetermined form with a known GL 210. A time interval 212 will pass after ingestion of the passes after ingestion of the known quality sugar in a predetermined form with a known GL 210 and the previously measured metabolism by the patient of the known quality sugar in a predetermined form with a known GL 202 is collected and can be used to tune the hypoglycemic protocol per subject (individualized) and set the hypoglycemic target range that is individualized. In some instances, the target range for example may be below 54 mg/dl and above 42 mg/dl and with a lower threshold of 40 mg/dl over a predetermined amount of time. In other instances, the target range for example may be below 45 mg/dl and above 38 mg/dl and with a lower threshold of 35 mg/dl over a predetermined amount of time. Based on at least two of the metabolic data (BGL, GSR, heart rate, SPO2, pupillary response, and temperature) collected from the subject prior to treatment the controller uses the measurements of the metabolic data during treatment to predictively adjust the infusions to maintain a prolonged duration near the lower hypoglycemic threshold for the individual via adjusting the infusion rate of insulin or adding glucose. The system is predictive and can use the slope of the curves of the sampled metabolic data during treatment to reduce insulin or add glucose prior to the subject falling below the lower threshold. In general, 30 mg/dl is a second threshold that should not be maintained, and the subject's BGL should not drop below that threshold. However, based on sensor collected data that level may be raised for a subject. By adding sensor data for at least one of temperature, GSR, SPO2, and heart rate the approach of BGL to a critical threshold can be predicted more accurately than only relying on BGL. This is especially true for the lower hypoglycemic threshold which should not be exceeded.

Pupillary response is an additional data point which, either by an imaging system also known as machine vision whereby pupil measurements are taken and input to a computing device and/or controller or human observation. The dilation change of the pupil can be used as an additional check on whether BGLs are too low.

FIG. 5 is a chart 400 of BGL ranges. It shows the optimal homeostatic range "A" for BGL and the larger range of BGL near a homeostatic range versus the precise range "C" needed for the prolonged hypoglycemic protocols disclosed herein. Range "D" shows the optimal range (a subset) within the target range and illustrates that there is very little margin for error when maintaining a subject for prolonged periods in the optimal non-homeostatic hypoglycemic range of about 30 mg/dl to about 38 mg/dl. Unlike the range for homeostatic BGL which has acceptable variation above and below the optional target range "A", for hypoglycemic protocols keeping as near as safely possible to the lower threshold "C" range for an individual subject needs predictive control and BGL measurements alone are insufficient to maintain that condition for prolonged periods. Our use if other metabolic data including GSR, temperature and heart rate allow for predictive control to maintain a subject in the target non-homeostatic hypoglycemic range "C" 30 mg/dl to less than about 50 mg/dl. If the subject's BGL falls below (or is predicted to fall below) the lower portion of the range "D" then an alert/alarm range "E" is reached and the controller sends out an alert or alarm.

During treatment of a subject several physiological data points of the subject such as BGL, GSR, SPO2 and temperature and pupillary response are monitored. An individual subject's data points for these physiological measurements collected by sensors and in future treatments are utilized to predictively maintain the subject's BGL at or near the lowest target of BGL for that individual for hypoglycemic protocols.

In use, (see FIG. 3) the controller starts the infusion of insulin 214, the controller starts the infusion of cocktail and/or adjuvant 216 and the sensors 110 measure the patient's GBL and measures vital signs 218. The skilled artisan or those of ordinary skill in the art will recognize that the sequence of infusing cocktail components, adjuvants, and the like before insulin or vice versa and/or any time gap between the infusions are variations of the disclosed process which are within the scope of this disclosure. A monitoring module 250 receives the measurements and the controller decisions if threshold levels are met for one or more of blood glucose levels (BGL) 262, oxygen 264 and vitals 266. If all threshold levels being monitored are met the then the controller continues the insulin infusion and cocktail/adjuvant infusions, and the system goes on to the timer module 275. If the BGL threshold 262 is not met then the controller will one or more of adjust insulin infusion, add glucose and alert via an alarm. If the O$_2$ threshold 264 is not met then the controller will one or more of adjust flow rate of the O$_2$ 150 delivered to patient, adjust one or more cocktail components 130, adjust infusion of one or more supplement/adjuvant components 140 flow rates, adjust other gaseous flow 160 and alert via an alarm. If the vitals threshold 266 is not met then the controller will one or more of adjust insulin infusion, adjust cocktail and/or adjuvant components infusion rates, add glucose and alert via an alarm. If threshold were not met then the sensors 110 measurements of the patient's blood glucose levels and measure of vital signs 218 are processed by the controller and the controller in the monitoring module 250 as described above decisions if the threshold are being met the monitoring and adjustments repeat.

In another exemplar, prior to treating the subject with the disclosed cocktail under hypoglycemic conditions, the patient consumes once again the predetermined quantity of a known quality sugar in a predetermined form with a known GL 210. A time interval 212 will pass after ingestion of the passes after ingestion of the known quality sugar in a predetermined form with a known GL 210 and the previously measured metabolism by the patient of the known quality sugar in a predetermined form with a known GL 202 is used at least in part by the controller to adjust insulin levels during the treatment. The controller starts the infusion of insulin 214, controller starts the infusion of one or more cocktail components 216 and the sensors 110 measure the patient's blood glucose levels and measures at least one of heart rate, GSR, and temperature. Optionally, oxygen levels may be measured.

A monitoring module 250 receives the measurements and the controller decisions if threshold levels are met for one or more of blood glucose levels (BGL) 262, oxygen 264 and vitals 266. If all threshold levels being monitored are met the then the controller continues the insulin infusion, and the system goes on to the timer module 275. If the BGL threshold 262 is not met then the controller will one or more of adjust insulin infusion, add glucose and alert via an alarm. If the O$_2$ threshold 264 is not met then the controller will one or more of the oxygen flow rate 150, adjust gaseous flow rate 160 of the O$_2$ delivered to subject, adjust one or more cocktail components 130, adjust infusion of one or more supplement/adjuvant components 140 flow rates and alert via an alarm. If the vitals threshold 266 is not met then the controller will one or more of adjust insulin infusion, adjust one or more of the cocktail and/or adjuvant infusion flow rates, add glucose and alert via an alarm. If threshold were not met then the sensors 110 measurements of the subject's blood glucose levels and measure of vital signs 218 are processed by the controller and the controller in the monitoring module 250 as described above decisions if the threshold are being met the monitoring and adjustments repeat. If threshold levels were met and insulin was continued then the system controller goes to the timer module 275. First elapsed infusion time is measured 278, if the time threshold is not met the measurements of one or more of BGL, O$_2$ saturation and vital signs are taken 280 and the controller in monitoring mode 250 processes the measurements and repeats the cycle. If the timer has met the threshold 300 the infusion of insulin is stopped and the infusion of cocktail components and/or adjuvant components 302 is stopped and the system measures one or more of BGL, O$_2$ saturation and other vital signs 310; the monitoring module 250 processes the measurements 350 to determine if the post insulin levels of two or more of BGL, O$_2$ saturation, and vital signs are met. If "yes", then the system stops. If the timer has met the threshold 300 the infusion of insulin is stopped and the infusion of cocktail components and/or adjuvant components 302 is stopped and the system measures two or more of BGL, GSR, heart rate and temperature the monitoring module 250 processes the measurements 350 to determine if the post insulin levels of the two or more of BGL, GSR, heart rate and temperature are met. If "yes", then the system stops. If "no" the system one or more of activates alarm and administers one or more of O$_2$ and glucose to the patient.

Figure 4:
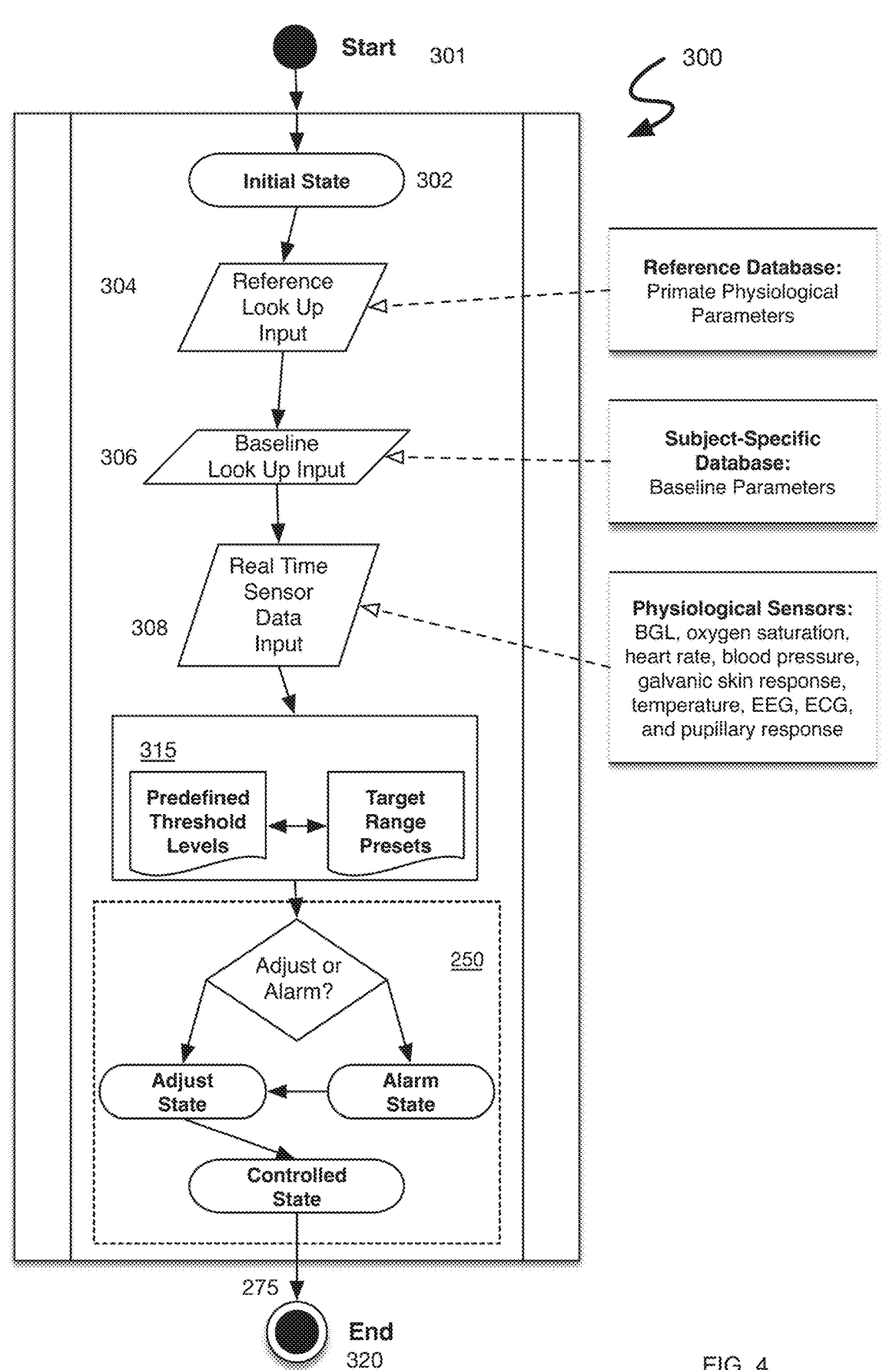
FIG. 4 illustrates aspects of a logic of the system logic.

FIG. 4 illustrates aspect of controller control logic for a system and method to control hypoglycemic conditions in a primate. It is an overview of some aspects of the operational flow of the control system 300. After the start 301 the controller is in the initial state 302 and will input data from at least on LUT and when available will input data from the primate's measured baseline 306. The input data from the LUT, which can be previously collected from the subject as described above, is compared with real time sensor inputs 308 (including sensors to measure BGL, oxygen saturation, heart rate, blood pressure, galvanic skin response, temperature, EEG, ECG, and pupillary response) and analyzed against predefined threshold or limits and/or target BGL range setting 315. The analysis continues in the monitoring module 250 (described in detail with reference to FIG. 3) wherein the control can predictively adjust the state of the subject by adjusting one or more of glucose, insulin, oxygen, and cocktail components being administered to main or keep the subject in the controlled optimal hypoglycemic (above threshold levels and within target range) and then enter timer module 275 if the timer has timed out end 320.

Examples

Cocktail agents for treating bacteria or virus in all instances, are use of controlled hypoglycemic conditions which support the use of lower toxicity cocktails and/or can enter the synovium more easily. Examples listed herein are not intended to be limiting. But rather, a solution of the disclosed delivery system is that the controlled induced hypoglycemic state improves delivery rates of cocktail and/or adjuvants to some bacterial and viruses.

Cocktail agents for treating bacteria or virus in all instances, are use of controlled hypoglycemic conditions which support the use of lower toxicity cocktails and/or can enter the dorsal root ganglion more easily. Examples listed herein are not intended to be limiting. But rather, a solution of the disclosed delivery system is that the controlled induced hypoglycemic state improves delivery rates of cocktail and/or adjuvants to some bacterial and viruses.

Exemplars of cocktail agent antibiotics useful for treating *Borrelia* and in particular *B. burgdorferi* include, but are not limited to clarithromycin, docycyclin, metronidazol. mezloxillian, piperacillin, azlocillin acylampicillin amoxicillin, cefuroxime, and Ceftriaxone.

Exemplars of cocktail agent antibiotics useful for treating herpes simplex virus (HSV) include, but are not limited to Acyclovir, Famciclovir, Valacyclovir and phenylbutyrate (PBA).

Examples of Cocktail or Adjuvant Components

One animal study provides evidence that the drug azlocillin completely kills off the disease-causing bacteria *Borrelia burgdorferi*. The study suggests it could also be effective for treating patients infected with drug-tolerant bacteria that may cause lingering symptoms (Pothineni, V. R., Potula, H H. S. K., Ambati, A. et al. Azlocillin can be the potential drug candidate against drug-tolerant *Borrelia burgdorferi* sensu stricto JLB31. Sci Rep 10, 3798 (2020). https://doi.org/10.1038/s41598-020-59600-4).

Quercetin is poorly soluble in water and unstable in physiological systems, and its bioavailability is very low. Quercetin is a flavonoid widely present in plants and has demonstrated pharmacological properties. Quercetin has also been shown to have antioxidant and anti-inflammatory effects. Lyme disease has inflammation associated with it.

Curcumin has been shown to Curcumin demonstrates significant benefits in the alleviation of arthritic inflammation and gut and brain inflammation. Curcumin exerts anti-inflammatory effects by blocking the activation of NF-κB, a pro-inflammatory signaling pathway heavily involved in Lyme-induced inflammation. In some instances, we have included 500 mg of curcumin in a 50 ml aqueous solution with 95% total curcuminoid content having 71% curcumin, in DMSO with Kolliphor HS 15 (also known as Macrogol 15 Hydroxystearate, Polyoxyl 15 Hydroxystearate) sodium citrate use only after dilution at least 1:10. The hydrophobic nature of curcumin presents challenges for bioavailability. A liposome with a mean particle size of about 200 nms composed of dipalmitoylphosphatidylcholine (Lipoid GMBH, Germany) and cholesterol (Carbogen Amcis B. V., The Netherlands) acts as a vehicle to deliver the curcumin at between about 250 mg and about 500 mg. In some instances, the curcumin may be ingested. In other instances, curcumin may be intravenously administered and can also be provided with a hydrophilic carrier.

We have applied a cocktail approach during hypoglycemic conditions of sequenced pharmaceutically effective doses of cocktail compounds to treat pathogenic infections.

The amount of insulin administered can be a function of pretreatment. When a patient consumes a known quality sugar in a predetermined form with a known glycemic Index (GI) and a known glycemic load (GL) measurement of the patient's innate systems response to the consumed material can be measured via blood glucose monitoring. Thereafter the controller uses the previously acquired measurements to set target or threshold blood glucose levels to adjust for during controlled hypoglycemic treatment. In operation the patient consumes the same known quality sugar in a predetermined form with a known glycemic Index (GI) and a known glycemic load (GL) at a predetermined time before the controlled hypoglycemic treatment. This system and method personalizes the hypoglycemic process to an individual thereby reducing the risk of insulin shock and seizure.

In general, with our system when the blood glucose level is dropping in a controlled and monitored fashion, we are able to have efficacious treatment with approximately 5-10% of the recommended dose over the same course of 45-60 minutes. The system disclosed herein is configured to sample the sensor data to closely monitor the patient. Before, during and after the system monitors hypoglycemic inducement measuring at least one of EKG, EEG, heart rate, blood pressure, oxygen saturation, glucose levels, pupillary response, temperature, electro galvanic skin resistance/response. The Galvanic Skin Response (GSR), also named Electrodermal Activity (EDA) and Skin Conductance (SC), is the measure of the continuous variations in the electrical characteristics of the skin, i.e., for instance the conductance, caused by the variation of the human body sweating. Sweating is correlated to the effect of the insulin and an indication of treatment progression and status. Optionally at least one of Vitamin C may be added to the IV, hydrogen gas, oxyhydrogen may be administered during or following the controlled hypoglycemic condition as a means to reduce inflammation in general. Although not listed in the flowing tables additional supplements and adjuvants may be included in the cocktail.

We have applied a combinatorial or cocktail approach of sequenced pharmaceutically effective doses of compounds to treat Lyme. We have observed that patients treated with an antihistamine (such as 4 mg Histakut) administered to also reduce cortisol has been observed in our treatment to reduce the effective dose of insulin required to treat. The antihistamine is followed by up to 1 gm Granisetron (to relieve nausea) and then an IV of 0.1-0.3 IU Insulin/kg bodyweight followed by a sequenced IV administration of three antibiotics. The antibiotic regime starts with 250-500 mg Metronidazol then 250 Docycyclin then 500 mg Clarithromycin to be sequence over about 45-to about 60 min followed by 250 cc Glucose 40% and also a glucose-based fluid or juice such Coke and/or Apple juice at 500 cc orally. The treatment is repeated 6-8 times over 2 months and the *Borrelia* and symptoms are reduced or eradicated. Those of ordinary skill in the art will recognize that antibiotics similar to Metronidazol, Docycyclin and Clarithromycin may be utilized in this treatment regime/sequence without departing from the scope of this invention and expect similar results under said hypoglycemic conditions and as such are within the scope of the disclosure. In some instances, azlocillin may be applied as the active agent in the cocktail alone or in combination with one or more of Metronidazol, Docycyclin and Clarithromycin. The mechanism includes insulin causing the membranes of cells to become more permeable, to allow for energy (glucose) in, the permeability is critical for getting the pharmaceutically effective compounds to the area the borreliosis is aggregated, those areas may include synovial membranes and extracellular matrices. In some instances, the borreliosis has been known to reside in the cerebral spinal fluid.

Those of ordinary skill in the art will recognize that antivirals agents which are in the same class as Acyclovir, Famciclovir, Valacyclovir and phenylbutyrate (PBA) may be substitute and expect similar results under said hypoglycemic conditions. It is preferable that Acyclovir is combined with phenylbutyrate (PBA). A combination of PBA with acyclovir cells infected with HSV-1, the drug combo was able to completely clear the virus from the cells faster and better than either drug alone. Acyclovir is also known to have toxic side effects in the kidneys. (Yadavalli, Tejabhiram & Suryawanshi, Rahul & Koganti, Raghuram & Hopkins, James & Ames, Joshua & Koujah, Lulia & Iqbal, Aqsa & Madavaraju, Krishnaraju & Agelidis, Alex & Shukla, Deepak. (2020). Standalone or combinatorial phenylbutyrate therapy shows excellent antiviral activity and mimics CREB3 silencing. Science Advances. 6. eabd9443. 10.1126/sciadv.abd9443.)

FIG. 6 Illustrates a component view of a hypoglycemic protocol sensor 500. In some instances the sensor has an adhesive interface 502 to attach it to the subject. The body of the sensor 504 supports one or more of a galvanic skin response (GSR) sensor 505, a temperature sensor 507, and a heart rate sensor 509. A transmitter 520 either through wireless communication protocols or via a wired 530 output 540 configured to transmit the sensor measurements and/or data. The transmitter communicates with at least one computing device which contains processors and processes the received data. The computing device may act as a controller to control at least one of the infusion of compounds being administered during prolonged hypoglycemic conditions, trigger alarms. The computing device will have a user interface to display the data communicated from the sensors and/or controller. In some instance the sensors may be on two or more adhesive devices. In some instance a BGL sensor 550 with an invasive contact 551 for insertion into a subject is also provided on the sensor.

A controller configured to receive and/or use the collected and transmitted data can compare it to data from the LUT, which can be previously collected from the subject as described above. This controller is configured to use the comparison with real time sensor inputs 308 to predictably adjust at least two of glucose, insulin and oxygen provided to the subject.

FIG. 7 illustrate measurements by sensor of values of vital signs. In the chart of FIG. 7 blood glucose levels (BGL) is shown trending from normal to controlled non-homeostatic hypoglycemic levels and the measurement of galvanic skin response (GSR) shows an increase preceding the fall in BGL at "X". The GSR shows a second rise at "Y". each rise may be sued to trigger an alert or alarm as described above. In response to an alert or alarm one or more of an observation and machine vision check on the subjects' pupillary response is used to verify subject status. This example of GSR is not meant as a limitation and other measurements including but not limited to other vital physiological signs may be used in conjunction with BGL and GSR to fine tune the control to maintaining non-homeostatic hypoglycemic levels.

FIG. 8 is an illustrations of the eye 600 before hypoglycemic protocols and the eye 600' during hypoglycemic protocols. The eye has a pupil "P1/P2", an iris 605, a scalera 610. A fixed size template 615 can be projected onto the eye to show the change in pupillary dilation from P1 to P2. That template may be used in conjunction with observation by human or with machine vision. Machine imaging sensors, known in the art, may also measure the diameter of the pupil and the change in that diameter to collect pupillary dilation change data to be input into a computing device or sensor. What is visible in FIG. 8 is that eye 600 has a pupillary size or dilation of P1 and eye 600' has a larger pupil size P2 corresponding to greater dilation. During hypoglycemic protocols to place the subject in a prolonged hypoglycemic non-homeostatic condition pupillary response (rate of dilation) and the amount of dilation are observable and/or measurable and may be used to one or more of fine tune the protocol per person or to set of alerts and or alarms.

The examples presented are not intended to be limiting and are nonlimiting examples of a few of the variety of cocktail components, including those that are toxic at the normally used dosages for treating bacteria or viruses, altering the cocktail sequence is within the scope of this disclosure. The exemplary implementations disclosed herein which can be used in provide for greater efficacy of cocktail components at low dose. In some instances, a cocktail component which can be toxic to a patient at the full recommended effective dosage are administered at less than 50% of the normal effective dosage and retain efficacy. In some instances, a cocktail component which can be toxic to a patient at the full recommended effective dosage can be administered at less than 40% of the normal effective dosage and retain efficacy. In some instances, a cocktail component which can be toxic to a patient at the full recommended effective dosage can be administered at less than 30% of the normal effective dosage and retain efficacy. In some instances, a cocktail component which can be toxic to a patient at the full recommended effective dosage can be administered at less than 20% of the normal effective dosage and retain efficacy. In some instances, a cocktail component which can be toxic to a patient at the full recommended effective dosage can be administered at 10% of the normal effective dosage and retain efficacy. In some instances, a cocktail component which can be toxic to a patient at the full recommended effective dosage can be administered at 5% or less of the normal effective dosage and retain efficacy.

While the compositions and method have been described in terms of what are presently considered to be the most practical and preferred implementations, it is to be understood that the disclosure need not be limited to the disclosed implementations. It will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A method to maintain prolonged hypoglycemic conditions to disrupt the homeostasis of synovial membranes, the method comprising:

a controller receiving blood glucose levels (BGL) measurements from a sensor configured to measure a subject's BGL;

the controller controlling delivery of insulin to the subject to lower blood glucose level measurements to a target non-homeostatic hypoglycemic range for BGL is 30 mg/dl to less than about 50 mg/dl;

the controller controlling delivery of glucose to the subject to maintain blood glucose levels within an optimal non-homeostatic hypoglycemic range;

reducing the amount of insulin required to reach target non-homeostatic hypoglycemic range by adding an antihistamine before or during antibiotic delivery, whereby the synovial membranes of the subject become more permeable to antibiotics used to treat Borreli; and, the controller controlling delivery of a cocktail of antibiotics to treat Borreli, when the subject's BGL is measured to be within the target non-homeostatic hypoglycemic range.

2. The method to maintain prolonged hypoglycemic conditions to disrupt the homeostasis of synovial membranes of claim 1 wherein the controller controlling delivery of at least one of glucose and insulin is configured to lower blood glucose level measurements to an optimal non-homeostatic hypoglycemic range between about 30 mg/dl and about 38 mg/dl.

3. The method to maintain prolonged hypoglycemic conditions to disrupt the homeostasis of synovial membranes of claim 1 wherein the antibiotics are at least one of clarithromycin, doxycycline, metronidazole, mezlocillin, piperacillin, azlocillin acylampicillin, amoxicillin, cefuroxime, and Ceftriaxone.

4. The method to maintain prolonged hypoglycemic conditions to disrupt the homeostasis of synovial membranes of claim 3, the method further comprising adding an adjuvant of one of Quercetin and Curcumin.

5. The method to maintain prolonged hypoglycemic conditions to disrupt the homeostasis of synovial membranes of claim 1 wherein the antibiotics are sequenced in time with each antibiotic administered separately before the next antibiotic is administered.

6. The method to maintain prolonged hypoglycemic conditions to disrupt the homeostasis of synovial membranes of claim 5 wherein the sequenced antibiotics are Metronidazole then Doxycycline then Clarithromycin.

7. The method to maintain prolonged hypoglycemic conditions to disrupt the homeostasis of synovial membranes of claim 1, the method further comprising:

the controller receives galvanic skin response (GSR) measurements from a sensor configured to measure a subject's GSR; and, the controller controlling delivery of insulin and glucose alters the amount or rate of insulin or glucose being delivered based on at least in part GSR measurements.

8. The method to maintain prolonged hypoglycemic conditions to disrupt the homeostasis of synovial membranes of claim 7, the method further comprising:

the controller receives heart rate measurements from a sensor on a subject configured to measure the subject's heart rate; and, the controller controlling delivery of insulin and glucose alters the amount or rate insulin or glucose is delivered based on at least in part GSR and heart rate measurements.

9. The method to maintain prolonged hypoglycemic conditions to disrupt the homeostasis of synovial membranes of claim 1, the method further comprising:

an observer checks pupillary dilation size before insulin is administered;

based on the periodic observer during prolonged hypoglycemic conditions the observer overrides the controller and at least one of administration of insulin is reduced, insulin administration is stopped, and glucose is administered.

10. The method to maintain prolonged hypoglycemic conditions to disrupt the homeostasis of synovial membranes of claim 1, the method further comprising:

an observer checks pupillary dilation size and inputs a value based on observation into the controller; and, the controller controlling delivery of insulin and glucose alters at least one of the insulin and glucose being administered based on at least in part on the pupillary value input.

11. The method to maintain prolonged hypoglycemic conditions to disrupt the homeostasis of synovial membranes of claim 1, the method further comprising:

machine vision periodically measures subject's pupillary change in size during prolonged hypoglycemic conditions which is input to the controller; and, the controller controlling delivery of insulin and glucose alters at least one of the insulin and glucose being administered based on at least in part on pupillary size inputs.

12. The method to maintain prolonged hypoglycemic conditions to disrupt the homeostasis of synovial membranes of claim 1, if the BGL is below the target non-homeostatic hypoglycemic range the controller is configured to trigger an alert or alarm.

13. The method to maintain prolonged hypoglycemic conditions to disrupt the homeostasis of synovial membranes of claim 12, wherein the alarm at least one of interrupt the delivery of insulin, delivers glucose, and delivers oxygen.

* * * * *